(12) United States Patent
Fujii

(10) Patent No.: US 7,074,746 B2
(45) Date of Patent: Jul. 11, 2006

(54) NAIL POLISH REMOVER

(75) Inventor: Gary Fujii, Rancho Palos Verdes, CA (US)

(73) Assignee: Biocerax, Inc., Los Angeles, CA (US)

( * ) Notice: Subject to any disclaimer, the term of this patent is extended or adjusted under 35 U.S.C. 154(b) by 0 days.

(21) Appl. No.: 10/804,834

(22) Filed: Mar. 19, 2004

(65) Prior Publication Data

US 2004/0224861 A1 Nov. 11, 2004

Related U.S. Application Data

(63) Continuation-in-part of application No. 10/394,405, filed on Mar. 19, 2003, now abandoned.

(51) Int. Cl.
*C11D 7/22* (2006.01)
*C11D 7/26* (2006.01)
*C11D 7/50* (2006.01)

(52) U.S. Cl. ............ 510/118; 510/505; 510/506; 424/61

(58) Field of Classification Search ........... 510/118, 510/201, 202, 473, 476, 499, 500, 505, 506
See application file for complete search history.

(56) References Cited

U.S. PATENT DOCUMENTS

| | | | | |
|---|---|---|---|---|
| 4,801,331 A | * | 1/1989 | Murase | 106/5 |
| 5,215,675 A | * | 6/1993 | Wilkins et al. | 510/206 |
| 5,258,070 A | | 11/1993 | Monteleone et al. | |
| 5,334,331 A | * | 8/1994 | Fusiak | 510/174 |
| 5,346,640 A | * | 9/1994 | Leys | 510/174 |
| 5,427,710 A | * | 6/1995 | Stevens | 134/1 |
| 5,464,555 A | * | 11/1995 | Bayless | 510/174 |
| 5,486,305 A | * | 1/1996 | Faryniarz et al. | 510/118 |
| 5,543,085 A | * | 8/1996 | Miner | 510/118 |
| 5,582,333 A | | 12/1996 | Bennett | |
| 5,827,807 A | | 10/1998 | Aoshima et al. | |
| 5,866,104 A | * | 2/1999 | Cataneo et al. | 424/61 |
| 6,071,867 A | | 6/2000 | Purcell et al. | |
| 6,103,682 A | | 8/2000 | Lallier | |
| 6,156,711 A | | 12/2000 | Perlman | |
| 6,187,108 B1 | * | 2/2001 | Machac et al. | 134/38 |
| 6,225,269 B1 | * | 5/2001 | Baker | 510/118 |
| 6,479,445 B1 | * | 11/2002 | Machac et al. | 510/206 |
| 6,689,727 B1 | * | 2/2004 | Olsson | 510/118 |
| 2004/0142830 A1 | * | 7/2004 | Tavares | 510/118 |

FOREIGN PATENT DOCUMENTS

WO    WO00/45776    *  8/2000

* cited by examiner

*Primary Examiner*—Gregory R. Del Cotto
(74) *Attorney, Agent, or Firm*—Pillsbury Wintrhop Shaw Pittman LLP

(57) ABSTRACT

A nail polish remover and methods of removing nail polish are provided, where the nail polish remover includes a least one heterocyclic solvent having a carbonyl group. A thickening agent may be included.

6 Claims, 2 Drawing Sheets

N-methylpyrrolidinone

Butyrolactone (BLO)

Ethylene Carbonate (EC)

US 7,074,746 B2

NAIL POLISH REMOVER

RELATED APPLICATIONS

This application is a continuation-in-part of U.S. patent application Ser. No. 10/394,405, filed Mar. 19, 2003, now abandoned, the entire contents of which are hereby incorporated by reference.

FIELD OF THE INVENTION

The present invention relates to removing nail polish from surfaces, in particular removing nail polish from fingernails or toenails.

BACKGROUND

Strong solvents are required to remove nail polish from a surface such as a fingernail or toenail, as the dried polish must be solubilized before removal. The most common solvent systems used to remove nail polish (also called nail lacquer or nail enamel) from fingernails or toenails have been acetone, ethyl acetate, methyl ethyl ketone, acetonitrile, and butyl acetate. However, these solvents have undesirable properties such as volatility, flammability, toxicity, and strong odor, as well as a tendency to irritate or desiccate skin and cuticle. Alternative formulations for removing nail polish have been developed by reducing or eliminating undesirable solvents, and/or by adding other agents with more desirable properties.

SUMMARY OF INVENTION

The present invention provides compositions and methods for removing nail polish using mixtures including an effective amount of at least one heterocyclic solvent having a carbonyl group.

A nail polish remover is provided having at least about 80 parts propylene carbonate (PC). Nail polish remover having at least about 80 parts PC and from about 0.1 to about 2.5 parts Vitamin E is provided herein. Nail polish remover having at least about 80 parts PC and from about 1 to about 10 parts of at least one oily solvent is provided herein, where the oily solvent includes, but is not limited to, methyl soyate or canola oil. Nail polish remover having at least about 80 parts PC and from about 1 to about 20 parts dipropylene glycol methyl ether (DPM) is provided herein. In one embodiment, the nail polish remover has about 80 parts PC and about 20 parts DPM. In another embodiment, the nail polish remover has about 85 parts PC and about 15 parts DPM. In another embodiment, the nail polish remover has about 90 parts PC and about 10 parts DPM. In another embodiment, the nail polish remover has about 95 parts PC and about 5 parts DPM. In another embodiment, the nail polish remover has about 99 parts PC and about 1 part DPM. Nail polish remover is provided having at least about 80 parts PC and from about 1 to about 20 parts DPM, and from about 0.1 to about 2.5 parts Vitamin E. Nail polish remover is provided having at least about 80 parts PC and from about 1 to about 20 parts DPM, and from about 1 to about 10 parts of at least one oily solvent, where the oily solvent includes, but is not limited to, methyl soyate or canola oil. In one embodiment, the nail polish remover has about 85 parts PC, about 10 parts DPM, and about 5 parts methyl soyate. In another embodiment, the nail polish remover has about 85 parts PC, about 10 parts DPM, about 5 parts methyl soyate, and about 0.5 parts Vitamin E. In one embodiment, the nail polish remover has about 85 parts PC, about 10 parts DPM, and about 5 parts canola oil. In another embodiment, the nail polish remover has about 85 parts PC, about 10 parts DPM, about 5 parts canola oil, and about 0.5 parts Vitamin E.

A nail polish remover is provided that includes an effective amount of a mixture of at least two heterocyclic solvents, each having a carbonyl moiety. Nail polish remover with an effective amount of a mixture including from about 25% v/v N-methyl pyrrolidinone (NMP) to about 75% v/v NMP and from about 25% v/v butyrolactone (BLO) to about 75% v/v BLO is provided herein. In one embodiment, the nail polish remover contains about 75% v/v NMP and about 25% v/v BLO. Nail polish remover with an effective amount of a mixture including from about 25% v/v NMP to about 75% v/v NMP and from about 25% v/v ethylene carbonate (EC) to about 75% v/v EC is provided herein. In one embodiment, the nail polish remover contains about 50% v/v NMP and about 50% v/v EC. Nail polish remover with an effective amount of a mixture including from about 25% v/v NMP to about 75% v/v NMP, and from about 25% v/v BLO to about 75% v/v BLO, and from about 25% v/v EC to about 75% v/v EC is provided herein. In one embodiment, the nail polish remover contains about 50% v/v NMP, about 25% v/v BLO, and about 25% v/v EC.

The nail polish remover as provided herein may further contain a thickening agent at a concentration of between about 0.1% w/v to about 5.0% w/v. The thickening agent may be selected from CARBOPOL® polymers or methylcelluloses. In one embodiment, the thickening agent is methylcellulose at a concentration of about 0.25% w/v. The nail polish remover as provided herein may be a gel.

A method of removing nail polish from a surface is provided herein, where the method includes: a) applying a nail polish remover to the surface, where the nail polish remover includes an effective amount of a mixture of at least one heterocyclic solvent, each having a carbonyl moiety; b) allowing the fingernail polish remover to solubilize the nail polish; and c) removing the solubilized nail polish from the surface. The method can be used to remove nail polish from a fingernail or a toenail.

A method for removing nail polish is provided wherein the heterocyclic solvents in the nail polish remover are pyrrolidinones, lactones, oxazolidinones, piperidones, hydantoin, cyclic carbonates, or cyclic ureas. A method for removing nail polish is provided wherein the heterocyclic solvents in the nail polish remover are propylene carbonate (PC), N-methyl pyrrolidinone (NMP), butyrolactone (BLO), or ethylene carbonate (EC).

The method can be carried out with a nail polish remover having at least about 80 parts propylene carbonate (PC). In one embodiment, the method is carried out using nail polish remover having about 80 parts propylene carbonate (PC) and from about 0.1 to about 2.5 parts Vitamin E. In one embodiment, the method is carried out using nail polish remover having about 80 parts propylene carbonate (PC) and from about 1 to about 10 parts of at least one oily solvent, where the oily solvent includes, but is not limited to, methyl soyate or canola oil. The method can be carried out with a nail polish remover having at least about 80 parts PC and from about 1 to about 20 parts dipropylene glycol methyl ether (DPM). In one embodiment, the method is carried out using nail polish remover having about 80 parts PC and about 20 parts DPM. In one embodiment, the method is carried out using nail polish remover having about 85 parts PC and about 15 parts DPM. In one embodiment, the method is carried out using nail polish remover having about 90 parts PC and about 10 parts DPM. In one embodiment, the method is carried out using nail polish remover having about 95 parts PC and about 5 parts DPM. In one embodiment, the method is carried out using nail polish remover having about 99 parts PC and about 1 part DPM. The method can be carried out using nail polish remover having at least about 80 parts PC, from about 1 to about 20 parts DPM, and from about 0.1 to about 2.5 parts Vitamin E. The method can be carried out using nail polish remover having at least about 80 parts PC, from about 1 to about 20 parts DPM, and from about 1 to about 10 parts of at least one oily solvent, where the oily solvent includes, but is not limited to, methyl soyate or canola oil. In one embodiment, the method is carried out using nail polish remover having about 85 parts PC, about 10 parts DPM, and about 5 parts methyl soyate. In another embodiment, the method is carried out using nail polish remover having about 85 parts PC, about 10 parts DPM, about 5 parts methyl soyate, and about 0.5 parts Vitamin E. In one embodiment, the method is carried out using nail polish remover having about 85 parts PC, about 10 parts DPM, and about 5 parts canola oil. In another embodiment, the method is carried out using nail polish remover having about 85 parts PC, about 10 parts DPM, about 5 parts methyl soyate, and about 0.5 parts Vitamin E.

The method can be carried out with nail polish remover including from about 25% v/v NMP to about 75% v/v NMP and from about 25% v/v BLO to about 75% v/v BLO. In one embodiment, the method is carried out using nail polish remover containing about 75% v/v NMP and about 25% v/v BLO. The method can be carried out with nail polish remover including from about 25% v/v NMP to about 75% v/v NMP and from about 25% v/v EC to about 75% v/v EC. In one embodiment, the method is carried out using the nail polish remover containing about 50% v/v NMP and about 50% v/v EC. The method can be carried out using nail polish remover including from about 25% v/v NMP to about 75% v/v NMP, from about 25% v/v BLO to about 75% v/v BLO, and from about 25% v/v EC to about 75% v/v EC. In one embodiment, the method is carried out using nail polish remover containing about 50% v/v NMP, about 25% v/v BLO, and about 25% v/v EC.

The method of removing nail polish remover as provided herein can be carried out using nail polish remover further including a thickening agent, where the thickening agent is present at a concentration of between about 0.1% w/v to about 5.0% w/v. The method can be carried out using a nail polish remover wherein the thickening agent a CARBOPOL® polymer or a methylcellulose. In one embodiment, the method is carried out using a nail polish remover wherein the thickening agent is methylcellulose at a concentration of about 0.25% w/v.

DETAILED DESCRIPTION OF THE INVENTION

Figure 1:
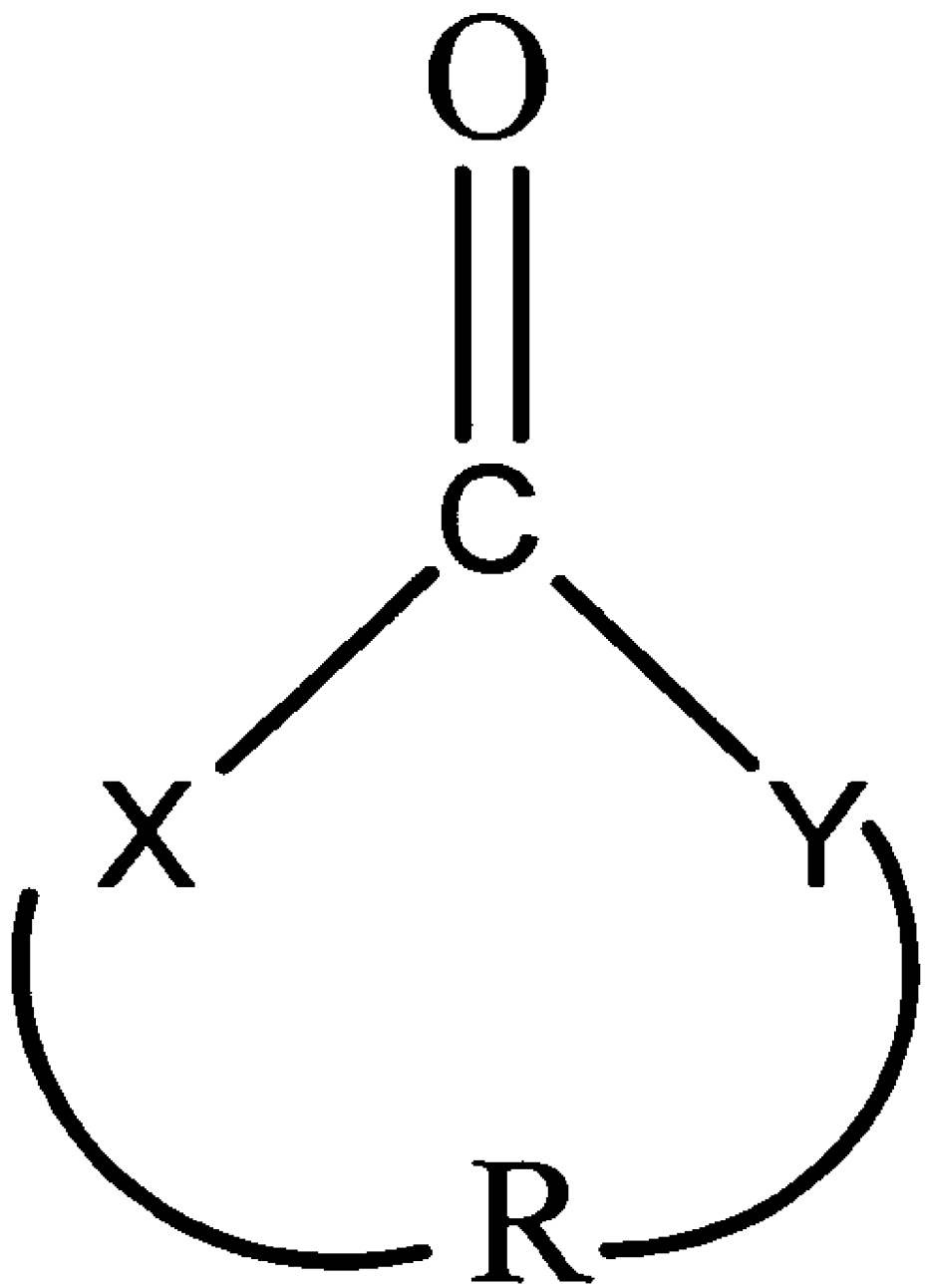
FIG. 1. Schematic of general molecular structure of heterocyclic solvents useful for removing nail polish. Position X=non-carbon atoms, especially O, N or S. Position Y=any of C, O, N or S. R=any combination of O, N, S, or $(CH_2)_n$ that completes the ring structure, where n=1–4. The ring structure can have side groups attached at various positions on the ring.
Figure 2:
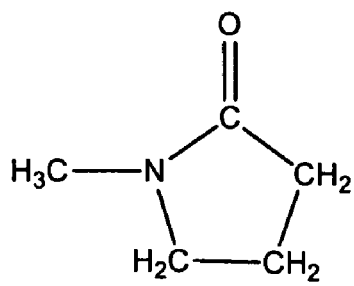
FIG. 2. Chemical structures of N-methyl pyrrolidinone (NMP), butyrolactone (BLO), and ethylene carbonate (EC)
Figure 2:
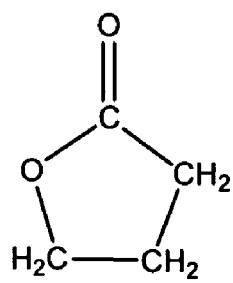
Figure 2:
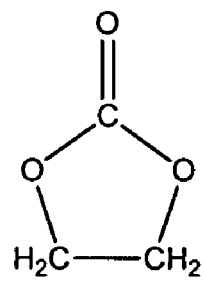

The present invention provides compositions and methods for removing nail polish using mixtures including at least one heterocyclic solvent having a carbonyl group. In one embodiment, at least two heterocyclic solvents are combined in a mixture such that an effective amount of the mixture rapidly and effectively removes nail polish as provided herein. Compositions and methods are provided for rapidly and completely removing nail polish, including removing multiple layers of nail polish or layers having different chemical compositions. Compositions provided herein have relatively low volatility and little or no odor, show low toxicity, are environmentally benign and are often biodegradable. Methods provided herein generate little or no odor, have low toxicity, and are very effective (e.g., nail polish remover provided herein can be applied in a thin layer). When used to remove nail polish from nails or skin, the compositions and methods of the present invention do not leave an oily or dry feeling on the skin, nor do they leave an unpleasant residual scent or odor.

The present invention provides compositions and methods for removing nail polish from a surface. In accordance with one aspect, the present invention provides compositions and methods for removing nail polish from a nail, where a nail includes but is not limited to a fingernail or toenail. The compositions and methods are rapid and effective, using a low-volatility and low-toxicity nail polish that does not irritate or dry the skin and cuticle, does not leave an oily residue, and does not have an unpleasant odor.

The term "nail polish" as used herein refers to materials commonly used for providing a protective and/or visual coating on fingernails and toenails, and encompasses materials known as nail polish, nail lacquer, nail polish-lacquer, nail enamel, and similar names. It is understood that nail polish can be applied to surfaces other than nails, and the compositions and methods provided herein can be used to remove nail polish from any surface having nail polish applied thereon. By way of example, the compositions and methods provided herein can be used for removing nail polish from surfaces including but not limited to skin, hair, clothing, shoes, handbags, jewelry, furniture, tables, counters, seats, equipment, or other surfaces with nail polish applied thereon.

The term "nail polish remover" as used herein refers to a composition capable of interacting with nail polish in such a way that application of nail polish remover to a surface having nail polish thereon permits removal of the nail polish from the surface. It is understood that nail polish remover will solubilize, dissolve, weaken, loosen, or otherwise disrupt the nail polish in such a way as to permit removal of the nail polish from the surface. The term "solubilize" is used generally herein to refer to the action of nail polish remover on nail polish, where the nail polish dissolves into the nail polish remover. The term "solubilized nail polish" is used generally herein to refer to the resulting mixture of nail polish and nail polish remover that can be removed from the surface. The term "removing nail polish" as used herein refers to application of nail polish remover to a surface having nail polish thereon, allowing the nail polish remover to solubilize the nail polish, and removing the resulting solubilized nail polish from the surface.

Application of the nail polish remover may be accomplished using any convenient method including but not limited to using a tissue (paper or non-cellulose tissue), a cotton ball, a sponge, a brush, or a stick to apply nail polish remover to a surface, or spraying or squeezing nail polish remover on a surface, or dipping a surface in nail polish remover (e.g., dipping a fingertip into a container with nail polish remover, in order to apply nail polish remover to a fingernail).

Following application of nail polish remover, the solubilized nail polish is removed from the surface. In one embodiment, the same material (e.g., tissue, cotton ball, sponge) is used to apply the nail polish remover to the surface and to remove the solubilized nail polish by wiping the surface, which can reduce waste. In another embodiment, unused material (e.g., tissue, cotton ball, sponge) is used to remove the solubilized nail polish from the surface. In yet another embodiment, the solubilized nail polish is removed by rinsing, dipping, dousing, spraying or submerging the surface using solutions including but not limited to nail polish remover, water, or other suitable solvents. It is understood that one of skill in the art can determine whether a particular nail polish remover is sufficiently water-miscible that water can be used to remove the solubilized nail polish. In one embodiment, a surface is submerged in nail polish remover and solubilized nail polish is removed by dispersion. In one embodiment, a surface is dipped in nail polish remover is then dipped in water and shaken to remove the solubilized nail polish from the surface. In another embodiment, nail polish remover is sprayed on a surface and the surface is rinsed with nail polish remover to remove the solubilized nail polish from the surface. In another embodiment, nail polish remover is sprayed on a surface and the surface is rinsed with water to remove the solubilized nail polish.

The time required for softening and loosening a nail polish coating varies with the heterocyclic solvent(s) being used, the total solvent strength of the nail polish remover, and the composition of the nail polish being removed. A coating may include multiple layers of nail polish. In a multilayer coating of nail polish, each layer may have a different chemical composition. In one embodiment, nail polish is removed about 15 seconds after application of nail polish remover to a surface. In another embodiment, nail polish is removed about 10 seconds after application. In yet another embodiment, nail polish is removed about 5 seconds after application. In another embodiment, nail polish is removed less than 5 seconds after application. In another embodiment, nail polish is removed almost immediately after application.

Compositions and methods for removing nail polish as disclosed herein are based on solvents that are heterocyclic and have a carbonyl moiety, where these solvents can function as aprotic polar solvents. The general molecular structure of the solvents used in the compositions and methods provided herein is illustrated in FIG. 1, where X=non-carbon atoms, especially O, N, or S, and Y=any of C, O, N or S, and R=any combination of O, N, S, or $(CH_2)_n$ that completes the ring structure, where n=1–4. The ring structure can have side groups, e.g., methyl groups, attached at various positions. Such molecules are typically water-miscible and have relatively low volatility. Compositions based on formulations of one or more of these solvents are intended to be safer alternatives to ketone or ester-based solvents which are flammable and often possess an unpleasant odor. Advantageously, these solvents are environmentally benign, have relatively low toxicity, and are miscible in water.

Examples of molecules suitable for use in the compositions and methods of the present invention include but are not limited to, pyrrolidinones, lactones, oxazolidinones, piperidones, hydantoin, cyclic carbonates, and cyclic ureas. Suitable pyrrolidinones (also known as pyrrolidones, based on the molecule known as 2-pyrrolidone, 2-pyrrolidinone, 2-oxopyrrolidine α-pyrrolidone or 2-ketopyrrolidine) include but are not limited to N-methyl pyrrolidinone (NMP, also known as 1-methyl-2-pyrrolidinone, N-methyl-α-pyrrolidinone, N-methyl-γ-butyrolactone, 1-methylazacyclopentan-2-one. MP, or M-Pyrol®). Suitable lactones include but are not limited to butyrolactone (BLO, also known as γ-butyrolactone (GBL)), valerolactone and thiobutyrolactone. Suitable oxazolidinones include but are not limited to 3-methyl-2-oxazolidinone. Suitable piperidones include but are not limited to 2-piperidone. Hydantoin (also known as 2,4-imidazolidinedione or glycolylurea) is likewise suitable. Suitable cyclized carbonates include but are not limited to ethylene carbonate (EC) and propylene carbonate (PC). Suitable cyclized ureas include ethylene urea and propylene urea.

With respect to the concentrations of various components provided herein, the term "% w/v" refers to the conventional calculation of weight/volume percent, i.e., the weight (in grams) of the component per 100 ml of solution. The term "% v/v" refers to the conventional calculation of volume percent or percent by volume, i.e., the volume of the solute divided by the sum of the volumes of the other component and multiplied by 100. The term "parts" refers to relative quantities of various components added to a formulation. One of skill in the art would understand the term "about" is used herein to mean that a concentration of "about" a recited percentage (%) of a component, or a formulation having "about" a recited number of parts of a component, produces the desired degree of effectiveness in the compositions and methods of the present invention. One of skill in the art would further understand that the metes and bounds of "about" with respect to the concentration of any component in an embodiment can be determined by varying the concentration of one or more components (by volume or by weight), determining the effectiveness of the mixture for each concentration, and determining the range of concentrations that produce mixtures with the desired degree of effectiveness in accordance with the present disclosure. The term "about" is further used to reflect the possibility that a mixture may contain trace components of other materials that do not alter the effectiveness or safety of the mixture.

The present invention provides compositions and methods for removing nail polish using heterocyclic solvents containing at least one carbonyl group. Accordingly, suitable formulations for use in compositions and methods as provided herein include formulations containing a single heterocyclic solvent or a mixture of heterocyclic solvents. In accordance with one aspect, the present invention provides an effective amount of a mixture of two or more heterocyclic solvents, each having at least one carbonyl group, where such a mixture provides effective compositions and methods for nail polish removal. In accordance with another aspect, the present invention provides a method of removing nail polish using an effective amount of the mixture of heterocyclic solvents. In another aspect of the invention, the present invention provides a nail polish remover including an effective amount of mixture of three heterocyclic solvents, each having at least one carbonyl group. In accordance with yet another aspect, the present invention provides a method of removing nail polish using an effective amount of a mixture of three heterocyclic solvents.

Heterocyclic solvents as used in the present invention may be undiluted or diluted. If diluted, a particularly useful diluent is water. Another useful diluent is glycerine. Another suitable diluent is dipropylene glycol methyl ether (DPM).

It will be understood that emollients, humectants, fragrances, coloring agents, and other components may be added to or used with the compositions and methods provided herein. Components that may be added include, but are not limited to, Vitamin E and oily solvents. Suitable forms of Vitamin E include, but are not limited to, tocopheryl acetate. Oily solvents are understood to include hydrophobic or amphiphilic compounds that solvate, or are miscible with, the heterocyclic solvents of the present invention. Suitable oily solvents include, but are not limited to, methyl soyate, canola oil, and other oily solvents derived from natural sources. It is understood that oily components such as Vitamin E or oily solvents, may have more than one function in the compositions and methods of the present invention. Oily components may serve as emollients or fragrances, and may improve the condition of the nail, or tissue surrounding the nail, from which polish is removed as provided. Oily components may also serve as solvents and/or gelling agents, depending on the other components present in a particular embodiment. One of skill in the art can identify oily components that impart the desired properties to compositions and methods of the present invention.

In accordance with one aspect of the present invention, a nail polish remover is provided which includes at least about 80 parts propylene carbonate (PC). In accordance with another aspect, a nail polish remover is provided which includes at least about 80 parts propylene carbonate (PC) and from about 0.1 to about 2.5 parts Vitamin E. In accordance with another aspect, a nail polish remover is provided which includes at least about 80 parts PC and from about 1 to about 10 parts of an oily solvent, where the oily solvent includes but is not limited to, methyl soyate and canola oil. In accordance with another aspect, a nail polish remover is provided which includes at least about 80 parts PC, from about 0.1 to about 2.5 parts Vitamin E, and from about 1 to about 10 parts of an oily solvent, where the oily solvent includes but is not limited to, methyl soyate and canola oil.

In accordance with one aspect of the present invention, a nail polish remover is provided which includes from about 80 to about 99 parts propylene carbonate (PC) and from about 1 to about 20 parts dipropylene glycol methyl ether (DPM). In one embodiment, the nail polish remover includes about 80 parts PC and about 20 parts DPM. In another embodiment, the nail polish remover includes about 85 parts PC and about 15 parts DPM. In another embodiment, the nail polish remover includes about 90 parts PC and about 10 parts DPM. In another embodiment, the nail polish remover includes about 95 parts PC and about 5 pails DPM. In another embodiment, the nail polish remover includes about 99 parts PC and about 1 part DPM.

In accordance with one aspect of the present invention, a nail polish remover is provided which includes from about 80 to about 99 parts propylene carbonate (PC), from about 1 to about 20 parts dipropylene glycol methyl ether (DPM), and from about 0.1 to about 2.5 parts Vitamin E (tocopheryl acetate). In one embodiment, the nail polish remover includes about 90 parts PC, about 10 parts DPM, and about 0.1 part Vitamin E. In another embodiment, the nail polish remover includes about 90 parts PC, about 10 parts DPM, and about 0.5 parts Vitamin E. In another embodiment, the nail polish remover includes about 90 parts PC, about 10 parts DPM, and about 1.0 parts Vitamin E. In another embodiment, the nail polish remover includes about 90 parts PC, about 10 parts DPM, and about 2.5 parts Vitamin E.

In accordance with one aspect of the present invention, a nail polish remover is provided which includes from about 80 to about 99 parts propylene carbonate (PC), from about 1 to about 20 parts dipropylene glycol methyl ether (DPM), and from about 1 to about 10 parts of at least one oily solvent, where the oily solvent includes, but is not limited to, methyl soyate and canola oil. In one embodiment, the nail polish remover includes about 85 parts PC, about 10 parts DPM, and about 5 parts methyl soyate. In one embodiment, the nail polish remover includes about 80 parts PC, about 10 parts DPM, and about 10 parts methyl soyate. In one embodiment, the nail polish remover includes about 85 parts PC, about 10 parts DPM, and about 5 parts methyl soyate. In one embodiment, the nail polish remover includes about 80 parts PC, about 10 parts DPM, and about 10 parts methyl soyate.

In accordance with another aspect of the present invention, a nail polish remover is provided which includes from about 80 to about 99 parts PC, from about 1 to about 20 parts DPM, from about 0.1 to about 2.5 parts Vitamin E, and from about 1 to about 10 parts oily solvent, where the oily solvent includes, but is not limited to, methyl soyate and canola oil. In one embodiment, the nail polish remover includes about 85 parts PC, about 10 parts DPM, about 5 parts methyl soyate, and about 0.5 parts Vitamin E. In another embodiment, the nail polish remover includes about 85 parts PC, about 10 parts DPM, about 5 parts canola oil, and about 0.5 parts Vitamin E.

In accordance with one aspect of the present invention, a nail polish remover is provided which includes from about 20% v/v N-methyl pyrrolidinone (NMP) to 100% v/v NMP. In one embodiment, the nail polish remover includes from about 25% v/v NMP to about 90% v/v NMP. In another embodiment, the nail polish remover includes from about 40% v/v NMP to about 80% v/v NMP. In another embodiment, the nail polish remover includes from about 50% v/v NMP to about 75% v/v NMP. In yet another embodiment, a nail polish remover in accordance with the present invention includes about 50% v/v NMP. In another embodiment, a nail polish remover in accordance with the present invention includes about 70% v/v NMP. In another embodiment, a nail polish remover in accordance with the present invention includes about 75% v/v NMP. In another embodiment, a nail polish remover in accordance with the present invention includes about 80% v/v NMP. In another embodiment, a nail polish remover in accordance with the present invention includes about 90% v/v NMP. In another embodiment, a nail polish remover in accordance with the present invention includes about 100% v/v NMP.

In accordance with another aspect of the invention, a nail polish remover is provided which includes from about 10% v/v butyrolactone (BLO) to 100% v/v BLO. In one embodiment, the nail polish remover includes from about 20% v/v BLO to about 75% v/v BLO. In another embodiment, the nail polish remover includes from about 25% v/v BLO to about 50% v/v BLO. In one embodiment, a nail polish remover in accordance with the present invention includes about 25% v/v BLO. In another embodiment, a nail polish remover in accordance with the present invention includes about 50% v/v BLO. In another embodiment, a nail polish remover in accordance with the present invention includes about 75% v/v BLO. In another embodiment, a nail polish remover in accordance with the present invention includes about 100% v/v BLO.

In accordance with yet another aspect of the invention, a nail polish remover is provided which includes from about 10% v/v ethylene carbonate (EC) to 100% v/v EC. In one embodiment, the nail polish remover includes from about 20% v/v EC to about 75% v/v EC. In another embodiment, the nail polish remover includes from about 25% v/v EC to about 50% v/v EC. In one embodiment, a nail polish remover in accordance with the present invention includes about 25% v/v EC. In another embodiment, a nail polish remover in accordance with the present invention includes about 50% v/v EC. In another embodiment, a nail polish remover in accordance with the present invention includes about 75% v/v EC. In another embodiment, a nail polish remover in accordance with the present invention includes about 100% v/v EC.

In one embodiment, the nail polish remover of the present invention includes a mixture of about 75% v/v NMP and about 25% v/v BLO. In another embodiment, the nail polish remover of the present invention includes a mixture of about 50% v/v NMP, about 25% v/v EC and about 25% v/v BLO. In yet another embodiment, the nail polish remover of the present invention includes a mixture of about 50% v/v NMP and about 50% v/v EC.

In accordance with another aspect of the invention, a nail polish remover is provided which includes from about 80 to about 99 parts propylene carbonate (PC) and from about 1 to about 20 parts ethylene carbonate (EC). In one embodiment, the nail polish remover includes about 80 parts PC and about 20 parts EC. In another embodiment, the nail polish remover includes about 85 parts PC and about 15 parts EC. In another embodiment, the nail polish remover includes about 90 parts PC and about 10 parts EC. In another embodiment, the nail polish remover includes about 95 parts PC and about 5 parts EC. In yet another embodiment, the nail polish remover includes about 99 parts PC and about 1 part EC.

Optionally, formulations suitable for use in the compositions and methods of the present invention include a thickening agent. A thickening agent can reduce the fluidity or "runniness" of a formulation, and helps the nail polish remover remain where it is applied (e.g., localized on the nail), which reduces the amount of nail polish remover needed and avoids spillage or misuse. The thickening agent is present in the composition in an amount sufficient to allow a layer of desired thickness to be applied to a fingernail or toenail. If desired, the thickening agent is present in the composition in an amount sufficient to prevent the nail polish from dripping or running off the nail. A variety of different thickeners may beneficially be used, and a combination of thickeners may be used if desired. Suitable thickening agents include but are not limited to methylcelluloses such as carboxymethylcellulose, hydroxymethylcellulose, hydroxyethylcellulose, hydroxypropyl methylcellulose, or CARBOPOL® polymers such as carboxypolymethylene (carbomer, carboxyvinyl polymer or other members of the "CARBOPOL®" group of water-soluble vinyl polymers). In one embodiment, the concentration of thickening agent or agents is from about 0.1% to 5% w/v. In another embodiment, the concentration of thickening agent or agents is from about 0.25% to about 0.5% w/v, still more preferably about 0.25% w/v. In another embodiment, the thickening agent is about 0.25% w/v methylcellulose.

If desired, the thickening agent is present in an amount sufficient to form a gel, wherein a gel is understood to be a semisolid system consisting of either suspensions of inorganic or organic molecules interpenetrated by a liquid. A variety of gelling agents can be used, including hydrophobic gelling agents (oleogels) such as liquid paraffin with polyethylene, or fatty oils gelled with colloid silica or aluminum or zinc soaps, or hydrophilic gelling agents (hydrogels) such as gels containing water, glycerol, or propylene glycol gelled with suitable gelling agents such as tragacanth, starch, cellulose derivatives, carboxyvinyl polymers and magnesium-aluminum silicates. (See, *Remington: The Science and Practice of Pharmacy*, 20$^{th}$ Edition, Gennaro et al. eds., Lippincott, Williams, and Wilkins, pages 745–747) Thickening agents as described above are suitable for use in formulating gels.

In accordance with another aspect of the present invention, a method for removing nail polish is provided which includes at least about 80 parts propylene carbonate (PC). In accordance with another aspect, a method for removing nail polish is provided which includes at least about 80 parts propylene carbonate (PC) and from about 0.1 to about 2.5 parts Vitamin E. In accordance with another aspect, a method for removing nail polish is provided which includes at least about 80 parts PC and from about 1 to about 10 parts of an oily solvent, where the oily solvent includes but is not limited to, methyl soyate and canola oil. In accordance with another aspect, a method for removing nail polish is provided which includes at least about 80 parts PC, from about 0.1 to about 2.5 parts Vitamin E, and from about 1 to about 10 parts of an oily solvent, where the oily solvent includes but is not limited to, methyl soyate and canola oil.

In accordance with one aspect of the present invention, a method for removing nail polish is provided which includes from about 80 to about 99 parts propylene carbonate (PC) and from about 1 to about 20 parts dipropylene glycol methyl ether (DPM). In one embodiment, the method for removing nail polish includes about 80 parts PC and about 20 parts DPM. In another embodiment, the method for removing nail polish includes about 85 parts PC and about 15 parts DPM. In another embodiment, the method for removing nail polish includes about 90 parts PC and about 10 parts DPM. In another embodiment, the method for removing nail polish includes about 95 parts PC and about 5 parts DPM. In another embodiment, the method for removing nail polish includes about 99 parts PC and about 1 part DPM.

In accordance with one aspect of the present invention, a method for removing nail polish is provided which includes from about 80 to about 99 parts propylene carbonate (PC), from about 1 to about 20 parts dipropylene glycol methyl ether (DPM), and from about 0.1 to about 2.5 parts Vitamin E (tocopheryl acetate). In one embodiment, the method for removing nail polish includes about 90 parts PC, about 10 parts DPM, and about 0.1 part Vitamin E. In another embodiment, the method for removing nail polish includes about 90 parts PC, about 10 parts DPM, and about 0.5 parts Vitamin E. In another embodiment, the method for removing nail polish includes about 90 parts PC, about 10 parts DPM, and about 1.0 parts Vitamin E. In another embodiment, the method for removing nail polish includes about 90 parts PC, about 10 parts DPM, and about 2.5 parts Vitamin E.

In accordance with one aspect of the present invention, a method for removing nail polish is provided which includes from about 80 to about 99 parts propylene carbonate (PC), from about 1 to about 20 parts dipropylene glycol methyl ether (DPM), and from about 1 to about 10 parts of at least one oily solvent, where the oily solvent includes, but is not limited to, methyl soyate and canola oil. In one embodiment, the method for removing nail polish includes about 85 parts PC, about 10 parts DPM, and about 5 parts methyl soyate. In one embodiment, the method for removing nail polish includes about 80 parts PC, about 10 parts DPM, and about 10 parts methyl soyate. In one embodiment, the method for removing nail polish includes about 85 parts PC, about 10 parts DPM, and about 5 parts methyl soyate. In one embodiment, the method for removing nail polish includes about 80 parts PC, about 10 parts DPM, and about 10 parts methyl soyate.

In accordance with another aspect of the present invention, a method for removing nail polish is provided which includes from about 80 to about 99 parts PC, from about 1 to about 20 parts DPM, from about 0.1 to about 2.5 parts Vitamin E, and from about 1 to about 10 parts oily solvent, where the oily solvent includes, but is not limited to, methyl soyate and canola oil. In one embodiment, the method for removing nail polish includes about 85 parts PC, about 10 parts DPM, about 5 parts methyl soyate, and about 0.5 parts Vitamin E. In another embodiment, the method for removing nail polish includes about 85 parts PC, about 10 parts DPM, about 5 parts canola oil, and about 0.5 parts Vitamin E.

In accordance with another aspect of the present invention, a method for removing nail polish from a surface is provided, wherein the method is carried out using a nail polish remover which includes from about 25% v/v N-methyl pyrrolidinone (NMP) to 100% v/v NMP. In one embodiment, the method is carried out using a nail polish remover which includes from about 40% v/v NMP to about 90% v/v NMP. In another embodiment, the method is carried out using a nail polish remover which includes from about 45% v/v NMP to about 80% v/v NMP. In another embodiment, the method is carried out using a nail polish remover which includes from about 50% v/v NMP to about 75% v/v NMP. In one embodiment, the method is carried out using a nail polish remover which includes about 50% v/v NMP. In another embodiment, the method is carried out using a nail polish remover which includes about 70% v/v NMP. In another embodiment, the method is carried out using a nail polish remover which includes about 75% v/v NMP. In another embodiment, the method is carried out using a nail polish remover which includes about 80% v/v NMP. In another embodiment, the method is carried out using a nail polish remover which includes about 90% v/v NMP. In another embodiment, the method is carried out using a nail polish remover which includes about 100% v/v NMP.

In accordance with another aspect of the present invention, a method for removing nail polish from a surface is provided, wherein the method is carried out using a nail polish remover which includes from about 25% v/v butyrolactone (BLO) to 100% v/v BLO. In one embodiment, the method is carried out using a nail polish remover which includes from about 25% v/v BLO to about 75% v/v BLO. In another embodiment, the method is carried out using a nail polish remover which includes from about 25% v/v BLO to about 50% v/v BLO. In one embodiment, the method is carried out using a nail polish remover which includes about 25% v/v BLO. In a another embodiment, the method is carried out using a nail polish remover which includes about 50% v/v BLO. In another embodiment, the method is carried out using a nail polish remover which includes about 75% v/v BLO. In another embodiment, the method is carried out using a nail polish remover which includes about 100% v/v BLO.

In accordance with yet another aspect of the present invention, a method for removing nail polish from a surface is provided, wherein the method is carried out using a nail polish remover which includes from about 25% v/v ethylene carbonate (EC) to 100% v/v EC. In one embodiment, the method is carried out using a nail polish remover which includes from about 25% v/v EC to about 75% v/v EC. In another embodiment, the method is carried out using a nail polish remover which includes from about 25% v/v EC to about 50% v/v EC. In one embodiment, the method is carried out using a nail polish remover which includes about 25% v/v EC. In another embodiment, the method is carried out using a nail polish remover which includes about 50% v/v EC. In another embodiment, the method is carried out using a nail polish remover which includes about 75% v/v EC. In another embodiment, the method is carried out using a nail polish remover which includes about 100% v/v EC.

In one embodiment, the method is carried out using a nail polish remover which includes an effective amount of a mixture of about 75% v/v NMP and about 25% v/v BLO. In another embodiment, the method is carried out using a nail polish remover which includes an effective amount of a mixture of about 50% v/v NMP, about 25% v/v EC and about 25% v/v BLO. In another preferred embodiment, the method is carried out using a nail polish remover which includes an effective amount of a mixture of about 50% v/v NMP and about 50% v/v EC.

In accordance with another aspect of the invention, a method for removing nail polish is provided which includes from about 80 to about 99 parts propylene carbonate (PC) and from about 1 to about 20 parts ethylene carbonate (EC). In one embodiment, the method for removing nail polish includes about 80 parts PC and about 20 parts EC. In another embodiment, the method for removing nail polish includes about 85 parts PC and about 15 parts EC. In another embodiment, the method for removing nail polish includes about 90 parts PC and about 10 parts EC. In another embodiment, the method for removing nail polish includes about 95 parts PC and about 5 parts EC. In yet another embodiment, the method for removing nail polish includes about 99 parts PC and about 1 part EC.

In accordance with one aspect of the invention, a method is provided that includes the steps of: a) applying nail polish remover to a nail or other surface having nail polish applied thereon, wherein the nail polish remover includes an effective amount of at least one heterocyclic solvent having a carbonyl moiety; (b) allowing the fingernail polish remover to solubilize the nail polish; and (c) removing the solubilized nail polish from the nail or other surface. In one embodiment, the method is used to remove nail polish from a nail. Steps may be repeated as necessary to accomplish full removal of the nail polish from the surface.

In accordance with another aspect of the invention, a method is provided that includes the steps of: a) applying a nail polish remover to a nail or other surface having nail polish applied thereon, wherein the nail polish remover includes an effective amount of a mixture of at least two heterocyclic solvents, each having a carbonyl moiety; (b) allowing the fingernail polish remover to solubilize the nail polish; and (c) removing the solubilized nail polish from the nail or other surface. In one embodiment, the method uses a nail polish remover that includes about 75% v/v NMP and about 25% v/v BLO in a mixture. In another embodiment, the method uses a nail polish remover that includes about 50% NMP and about 50% EC in a mixture. In yet another embodiment, the method uses a nail polish remover that includes about 50% v/v NMP, about 25% v/v EC and about 25% v/v BLO in a mixture.

It will be understood that emollients, humectants, fragrances, coloring agents, and other components may be added to or used with the compositions and methods provided herein. One of skill in the art can select additional components and determine suitable amounts and formulations such that the final composition functions with the desired degree of effectiveness to remove nail polish as provided herein.

EXAMPLES

Example 1

Evaluation of Solvents and Mixtures of Solvents for Ability to Rapidly Remove Nail Polish Candidate solvents NMP, BLO, and EC were selected and tested for the ability to rapidly remove nail polish. Undiluted solvents and solvent mixtures were tested as shown in Table 1, below. Tests were conducted as blind side-by-side comparison studies with several volunteer test subjects. Each test was conducted by applying each sample of nail polish remover to one of the test subject's nails that was coated with nail polish. The nail polish was removed with either a tissue or with a cotton ball. Results are listed in Table 1 below, where a single plus sign indicates that the nail polish remover formulation works to remove nail polish, and a double plus sign indicates those formulations most preferred by the test subjects.

TABLE 1

| Solvent | Subject 1 | Subject 2 | Subject 3 |
|---|---|---|---|
| N-methylpyrrolidinone (NMP) | + | + | + |
| Butyrolactone (BLO) | + | + | + |
| Ethylene carbonate (EC) | + | + | + |
| NMP:BLO 75:25 | + | + | + |
| NMP:BLO 50:50 | + | + | + |
| NMP:BLO 25:75 | + | + | + |
| NMP:EC 75:25 | + | + | + |
| NMP:EC 50:50 | + | ++ | ++ |
| NMP:EC 25:75 | + | + | + |
| BLO:EC 75:25 | + | + | + |
| BLO:EC 50:50 | + | + | + |
| BLO:EC 25:75 | + | + | + |
| NMP:BLO:EC 50:25:25 | ++ | ++ | ++ |
| NMP:BLO:EC 25:50:25 | + | + | + |
| NMP:BLO:EC 25:25:50 | + | + | + |

The results presented in Table 1 showed that all three solvents tested (NMP, BLO, EC) rapidly removed nail polish. Each solvent worked well in undiluted form, and as did mixtures of two or three solvents. Depending on the type of nail polish used by each test subject, the time required to remove nail polish varied from almost immediately (5 seconds or less) to approximately 15 seconds. Although each formulation removed nail polish, the formulation containing 75% NMP and 25% BLO worked best to rapidly and completely remove nail polish. In addition, formulations containing 50% NMP and 25–50% EC were preferred by test subjects who reported that these formulations did not leave an oily or dry feeling to the skin and did not leave any residual scent or odor. The formulation containing 50% v/v NMP, 25% v/v EC, and 25% v/v BLO was most preferred by test subjects.

Example 2

Evaluation of Diluents

Various diluents were tested to determine their effect on the ability of NMP to remove a standard nail polish (Nail Savvy #716 Santa Fe Mauve). NMP was diluted with water to generate solutions having from 100% NMP to 50% NMP. Each solution was tested by dipping a tissue or cotton ball into the solution and rubbing the tissue or cotton ball on a finger nail to which Nail Savvy #716 Santa Fe Mauve had been applied. Two results were determined in each test: whether the solution removed the nail polish, and how long it took to remove the nail polish. Results are shown in Table 2. Aqueous NMP solutions of 50% did not remove nail polish. Solutions of 60% to 70% NMP in water were able to remove nail polish, but the process was slow. Aqueous NMP solutions of 80% or higher removed nail polish rapidly (less than five seconds).

TABLE 2

| NMP | Water | Removal | Time |
|---|---|---|---|
| 100% | 0% | Yes | <5 seconds |
| 90% | 10% | Yes | <5 seconds |
| 80% | 20% | Yes | <5 seconds |
| 70% | 30% | Yes | 5–10 seconds |
| 60% | 40% | Yes | >10 seconds |
| 50% | 50% | No | Not determined |

Other diluents were also tested. NMP was diluted in diethanolamine, glycerin, and Dowanol® PM (propylene glycol methyl ether) and tested for the ability to remove nail polish (Nail Savvy #716 Santa Fe Mauve). Results are shown in Table 3.

TABLE 3

| Solvent | Diluent | % Diluent | Removal |
|---|---|---|---|
| NMP | Diethanolamine | 20% | Yes |
| NMP | Diethanolamine | 50% | Not too well |
| NMP | Glycerine | 20% | Yes |
| NMP | Dowanol PM | 20% | Not too well |

Although formulations of NMP diluted in diethanolamine, glycerine, and dowanol PM worked to remove nail polish, the effectiveness varied, and undiluted NMP was preferred by test subjects.

Example 3

Addition of Thickening Agent

Using 75% v/v NMP in water as a basic formulation, a series of solutions were prepared with varying amounts of thickening agents. Solutions ranging from 0.25% to 1.0% w/v CARBOPOL® polymer or methylcellulose in an aqueous solution of 75% v/v NMP were tested for their ability to remove nail polish. The test was conducted by brushing nail polish remover onto test subject's nails and after approximately ten (10) seconds, nail polish was removed using either a tissue or a cotton ball. The preferred thickness of each the solutions was also determined. Results are shown in Table 4.

TABLE 4

| Thickening agent | Water | Comments |
|---|---|---|
| CARBOPOL ® | 1.0% | Too thick |
| CARBOPOL ® | 0.5% | Too thick |
| CARBOPOL ® | 0.25% | Good |
| Methycellulose | 1.0% | Too thick |
| Methylcellulose | 0.50% | Good |
| Methylcellulose | 0.25% | Good |

All thickened formulations removed nail polish. Occasionally, a second application of nail polish remover was needed to completely remove all traces or spots of polish that were missed on the first removal. Solutions of 1.0% w/v CARBOPOL®, 0.5% w/v CARBOPOL® and 1.0% w/v methylcellulose were considered too thick by the test subjects. Solutions of 0.25% w/v CARBOPOL®, 0.25% w/v methylcellulose, and 0.5% w/v methylcellulose had a favorable thickness. The thickness of the 0.25% w/v methylcellulose solution was slightly preferred over the 0.5% w/v methylcellulose solution.

Example 4

Nail Polish Remover Formulations Containing Propylene Carbonate

Compositions including propylene carbonate (PC), dipropylene glycol methyl ether (DPM), and other additives, were tested for the ability to rapidly remove nail polish. PC and DPM are approved solvents for use in cosmetics. PC/DPM formulations containing varying amounts and combinations of Vitamin E (tocopheryl acetate) and natural oil based solvents derived from soy beans (methyl soyate) and canola oil, were tested for their ability to rapidly remove nail polish. Table 5, below, shows formulations that were tested, where the quantities of each component added is expressed as "parts" of the whole formulation.

TABLE 5

| Propylene carbonate (PC) | Dipropylene glycol methyl ether (DPM) | Methyl Soyate | Canola Oil | Vitamin E | Comments |
|---|---|---|---|---|---|
| A. Formulations with PC and DPM alone | | | | | |
| 80 | 20 | | | | Works fine; slight odor |
| 90 | 10 | | | | Works fine; slight odor |
| 95 | 5 | | | | Works fine; slight odor |
| B. Formulations with PC, DPM, and Vitamin E | | | | | |
| 90 | 10 | | | 0.5 | Works fine; slight odor |
| 90 | 10 | | | 0.1 | Works fine; slight odor |
| 90 | 10 | | | 1 | Works fine; slight odor |
| 90 | 10 | | | 2.5 | Phases separate |
| C. Formulations with PC, DPM, methyl soyate, and canola oil | | | | | |
| 85 | 10 | 5 | | | Works fine; slight odor |
| 85 | 10 | | 5 | | Works fine; slight odor |
| 80 | 10 | 10 | | | Phases separate |
| 80 | 10 | | 10 | | Phases separate |
| D. Formulations with PC, DPM, methyl soyate, canola oil, and Vitamin E | | | | | |
| 85 | 10 | 5 | | 0.5 | Works fine; slight odor |
| 85 | 10 | | 5 | 0.5 | Works fine; slight odor |

As shown in Table 5A, formulations containing PC, and DPM up to 20 parts, were effective at removing nail polish. As shown in Table 5B, formulations containing 90 parts PC, 10 parts DPM, and Vitamin E (tocopheryl acetate) up to 2.5 parts were effective at removing nail polish. As shown in Table 5C, oil solvents derived from natural sources (methyl soyate and canola oil) up to 10 parts were effective at removing nail polish, but phase separation was seen when 10 parts oily solvent was added. As shown in Table 5D, Vitamin E can be added to formulations containing methyl soyate or canola oil, and the resulting formulations are effective at removing nail polish.

The foregoing descriptions and examples illustrate selected embodiments of the present invention and in light thereof various modifications will be suggested to one of skill in the art, all of which are in the spirit and purview of this invention.

What is claimed is:

1. A nail polish remover comprising at least about 80 parts propylene carbonate, from about 0.1 to about 2.5 parts Vitamin E, and from about 1 to about 10 parts of canola oil.

2. A nail polish remover comprising at least about 80 parts propylene carbonate, from about 1 to about 20 parts dipropylene glycol methyl ether, and from about 0.1 to about 2.5 parts Vitamin E, and from about 1 to about 10 parts of canola oil.

3. A nail polish remover comprising at least about 80 parts propylene carbonate, from about 1 to about 20 parts dipropylene glyco methylether, from about 1 to about 10 parts of canola oil, and about 0.5 parts Vitamin E.

4. A nail polish remover comprising at least about 80 parts propylene carbonate, from about 1 to about 20 parts dipropylene glycol methylether, and from about 1 to about 10 parts canola oil.

5. The nail polish remover of claim 4, comprising about 85 parts propylene carbonate, about 10 parts dipropylene glycol methylether, and about 5 parts canola oil.

6. The nail polish remover of claim 4, further comprising about 0.5 parts Vitamin E.

* * * * *